United States Patent [19]

Löwenadler et al.

[11] Patent Number: 5,411,732
[45] Date of Patent: May 2, 1995

[54] PREPARATION OF FUSED PROTEINS, ANTIBODIES AND PROCESSES THEREFORE

[75] Inventors: Björn Löwenadler, Solna; Erik Holmgren, Lidingö; Mathias Uhlén, Upsala, all of Sweden; Björn Nilsson, Foster City, Calif.

[73] Assignee: Kabi Pharmacia Aktiebolag, Upsala, Sweden

[21] Appl. No.: 130,430

[22] Filed: Oct. 1, 1993

Related U.S. Application Data

[63] Continuation of Ser. No. 596,319, Oct. 12, 1990, abandoned, which is a continuation of Ser. No. 42,117, Apr. 24, 1987, abandoned.

[30] Foreign Application Priority Data

Apr. 25, 1986 [SE] Sweden ................................ 8601940

[51] Int. Cl.⁶ ...................... A61K 39/00; C12N 15/00
[52] U.S. Cl. ........................ 424/192.1; 424/184.1; 435/69.7; 435/69.3; 435/172.3; 435/320.1; 935/12; 935/47
[58] Field of Search ............... 424/184.1, 192.1; 435/69.3, 192.2, 172.3, 69.7, 320.1; 935/12, 47

[56] References Cited

U.S. PATENT DOCUMENTS 4,703,004 10/1987 Hopp et al. ............................ 435/68
4,707,358 11/1987 Kieft et al. ............................ 424/89

FOREIGN PATENT DOCUMENTS

WO84/03103 8/1984 WIPO.
85/04654 10/1985 WIPO.
85/05037 11/1985 WIPO.
86/06635 11/1986 WIPO.

OTHER PUBLICATIONS

"Antigen Engineering in Yeast: Synthesis and Assembly of Hybrid Hepatitis B Surface Antigen-Herpes Simplex 1 gD Particles", Valenzuela, Bio/Technology, vol. 3, pp. 323–325.
"Fusion of Secreted Proteins to Alkaline Phosphatase: An Approach for Studing Protein Secretion", Hoffman, Proc. Natl. Acad. Sci, vol. 82, pp. 5107–5111.
Nilsson et al. (A), EMBO Journal 4:1075–80 (1985).
Nilsson et al. (B), Nuc. Acid Res. 13:1151–72 (1985).
Uhlen et al., J. Bacteriology 159:713–719 (1984).
Spindler et al., J. Virology 49:132–141 (1984).
Reed, Gene 20:255–265 (1982).
Mole et al., J. Virology 54:703–710 (1985).
Sugita et al., J. Biochemistry 97:1247–1250 (1985).
Broekhuijsen et al., Gene 49:189–197 (1986).
Weir et al., J. Virology 56:534–540 (1985).
Kökler et al., Nature 256:495–497 (1975).

Primary Examiner—Jasemine C. Chambers
Attorney, Agent, or Firm—Burns, Doane, Swecker & Mathis

[57] ABSTRACT

A process for preparing antibodies specific for an amino acid sequence which comprises immunizing a mammal with a fused protein comprising said amino acid sequence fused to an immunogenic IgG binding protein is disclosed.

10 Claims, 6 Drawing Sheets

ZZ-IGF-1        894    BASES

```
1         11        21        31        41        51
TCGAAATAGCGTGATTTTGCGGTTTTAAGCCTTTTACTTCCTGAATAAATCTTTCAGCAA 61        71        81        91        101       111
AATATTTATTTTATAAGTTGTAAAACTTACCTTTAAATTTAATTATAAATATAGATTTTA 121       131       141       151       161       171
GTATTGCAATACATAATTCGTTATATTATGATGACTTTACAAATACATACAGGGGGTATT 181       191       201       211       221       231
AATTTGAAAAAGAAAAACATTTATTCAATTCGTAAACTAGGTGTAGCTATTGCATCTGTA
          LeuLysLysLysAsnIleTyrSerIleArgLysLeuGlyValGlyIleAlaSerVal 241       251       261       271       281       291
ACTTTAGGTACATTACTTATATCTGGTGCCGTAACACCTGCTGCAAATGCTGCGCAACAC
ThrLeuGlyThrLeuLeuIleSerGlyGlyValThrProAlaAlaAsnAlaAlaGlnHis
                            The signal sequence ◄──► Cleavage region 301       311  AccI  321       331       341       351
GATGAAGCCGTAGACAACAAATTCAACAAAGAACAACAAAACGCGTTCTATGAGATCTTA
AspGluAlaValAspAsnLysPheAsnLysGluGlnGlnAsnAlaPheTyrGluIleLeu
             └──► Z-region 361       371       381       391       401       411
CATTTACCTAACTTAAACGAAGAACAACGAAACGCCTTCATCCAAAGTTTAAAAGATGAC
HisLeuProAsnLeuAsnGluGluGlnArgAsnAlaPheIleGlnSerLeuLysAspAsp 421       431       441       451       461       471
CCAAGCCAAAGCGCTAACCTTTTAGCAGAAGCTAAAAAGCTAAATGATGCTCAGGCGCCG
ProSerGlnSerAlaAsnLeuLeuAlaGluAlaLysLysLeuAsnAspAlaGlnAlaPro 481 AccI   491       501       511       521       531
AAAGTAGACAACAAATTCAACAAAGAACAACAAAACGCGTTCTATGAGATCTTACATTTA
LysValAspAsnLysPheAsnLysGluGlnGlnAsnAlaPheTyrGluIleLeuHisLeu
       └──► Z-region 541       551       561       571       581       591
CCTAACTTAAACGAAGAACAACGAAACGCCTTCATCCAAAGTTTAAAAGATGACCCAAGC
ProAsnLeuAsnGluGluGlnArgAsnAlaPheIleGlnSerLeuLysAspAspProSer 601       611       621       631       641       651
CAAAGCGCTAACCTTTTAGCAGAAGCTAAAAAGCTAAATGATGCTCAGGCGCCGAAAGTA
GlnSerAlaAsnLeuLeuAlaGluAlaLysLysLeuAsnAspAlaGlnAlaProLysVal 661   EcoRI 671       681       691       701       711
GACGCGAATTCTAACGGTCCCGAAACTCTGTGCGGTGCTGAACTGGTTGACGCTCTGCAG
AspAlaAsnSerAsnGlyProGluThrLeuCysGlyAlaGluLeuValAspAlaLeuGln
           └──► IGF-1

721       731       741       751       761       771
TTTGTTTGCGGTGACCGTGGTTTTTATTTTAACAAACCCACTGGTTATGGTTCTTCTTCT
PheValCysGlyAspArgGlyPheTyrPheAsnLysProThrGlyTyrGlySerSerSer 781       791       801       811       821       831
CGTCGTGCTCCCCAGACTGGTATTGTTGACGAATGCTGCTTTCGTTCTTGCGACCTGCGT
ArgArgAlaProGlnThrGlyIleValAspGluCysCysPheArgSerCysAspLeuArg 841       851       861       871       881       891 HindIII
CGTCTGGAAATGTATTGCGCTCCCCTGAAACCCGCTAAATCTGCTTAGAAGCTT
ArgLeuGluMetTyrCysAlaProLeuLysProAlaLysSerAla***
```

PREPARATION OF FUSED PROTEINS, ANTIBODIES AND PROCESSES THEREFORE

This application is a continuation of application Ser. No. 07/596,319, filed Oct. 12, 1990, now abandoned, which is a continuation of application Ser. No. 07/042,117, filed Apr. 24, 1987, now abandoned.

The present invention relates to a process for preparing a fused protein comprising an amino acid sequence fused to an immunogenic carrier protein. The invention also covers a process for the preparation of polyclonal antibodies using the fused protein thus prepared, as well as the use of the fused protein as a vaccin.

In accordance with the present invention a gene encoding a desired amino acid sequence is isolated, synthesized or otherwise obtained. The so obtained DNA fragment is inserted into a bacterial expression vector in such a way that it becomes joined in phase to a DNA part encoding the carrier protein sequence as well as other regulatory sequences needed for high level expression in a host cell.

The DNA segment encoding the functional protein parts are ideally digested with an appropriate restriction enzyme or are otherwise manipulated to generate cohesive or blunt termini to facilitate ligation with each other and with a plasmid or other type of cloning vector.

To carry out the present invention, various cloning and expression vectors may be utilized. Although the preference is for a plasmid, the vector may be of bacteriophage or cosmid origin, when used in bacteria. If cloning takes place in a mammalian or plant cell a virus derivative can be used as a vector. If a plasmid is employed, it may be obtained from a natural source or artificially synthesized. The particular plasmid chosen should be compatible with the particular cell serving as a host.

Various procedures and materials for preparing recombinant vectors, transforming transfecting or protoplast fusing host cells with the vectors, replicating the vector and expressing polypeptides and proteins are discussed in the following references:

Old and Primrose, *Principle of Gene Manipulation*, (2nd Ed. 1981).
Maniatis et.al. Molecular cloning, a laboratory manual. Cold Spring Harbor laboratory (1982).
Silhavy et.al. Experiments with gene fusions. Cold Spring Harbor laboratory (1984).
Methods in Enzymology Eds. Wu et.al. volumes 68, 100, 101, Recombinant DNA parts A, B and C, Acad. Press, which disclosures are incorporated herein by reference.

The present invention sets out to provide a process whereby specific antibodies can be made against any given amino acid sequence fused to an immunogenic carrier protein after expression in a transformed host cell. More specifically the present invention deals with the production of antibodies against the desired amino acid sequence be it a protein, a peptide or a short stretch of amino acids. Antibodies may be generated by immunizing mice, rabbits or other appropriate animals with the fusion protein. The carrier molecule provides facilitated recognition of the desired peptide by the immune system of the inoculated animals. Using a carrier molecule with polyclonal B-cell stimulatory effect may further enhance the immune response in the immunized hosts.

One equally important aspect of the present invention concerns the generation of vaccines for human or animal use by expression of cloned or synthesized DNA segments encoding protein parts fused to the carrier protein, that may confer neutralizing activity against viral, bacterial or other infectious agents after inoculation.

In this context a synthetic oligonucleotide encoding an atigenic determinant portion of a natural protein is fused to the gene encoding the carrier protein.

When the formed hybrid protein is introduced into the desired host, it initiates the production of antibodies or a cell mediated response in the host to the aforesaid antigenic determinant portion of the natural protein. The method of manufacturing vaccines, comprises the steps of determining from the protein or DNA sequence (cDNA sequence if one host genome is RNA) of the organism in question the amino acid sequence of an antigenic determinant portion of a protein antigen. Synthesizing a oligonucleotide segment encoding a peptide which antigenically is the duplicate or substantial duplicate of the determinant portion of the protein. Introducing the DNA segment encoding the antigenic peptide portion into an expression vector expressing a hybrid protein consisting of a carrier conjugated to the antigenic peptide.

The plasmids used for expression and the host system which under controlled growth secretes the hybrid protein to the outside medium have been thoroughly described in Swedish Patent Appln. 8505921-0, filing date 85.12.17 "A method to export gene products to the growth medium of gram negative bacteria and Swedish Patent Appln. 8505922-8 filing date 85.12.17 "Construction of an IgG-binding protein to facilitate downstream processing using protein engineering), which disclosures are incorporated herein by reference.

The hybrid protein constitutes a carrier and the desired protein. The carrier is preferably an IgG binding protein, hereafter referred to as immunoglobulin binding protein (IGB) such as *Staphylococcus aureus* protein A, a protein A related protein such as Z-protein as defined in Swedish Patent Appln. 8505922-8 or Streptococcal protein G.

Figure 1:
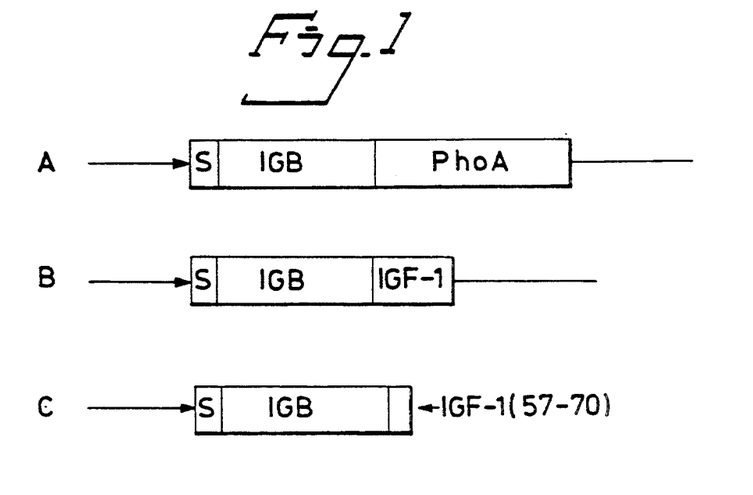
FIG. 1 shows a schematic representation of the fusion proteins described in Examples 1 to 3. S represents the protein A signal sequence, IGB represents an IgG binding domain.

The desired protein can be purified as a fusion protein to the carrier (IGB) (FIG. 1) and can thus be purified in a single step using IgG affinity chromatography (FIG. 8). The desired protein can be part of or the whole polypeptide (such as a hormon) or combinations of different polypeptides. Both the amino terminal end and/or the carboxyl-terminal end of the desired protein can be fused to the carrier.

Due to the fact that all the manipulating steps are performed at the DNA level, to fuse the carrier to the desired protein, any polypeptide can be produced. The methods used routinely in molecular biology for fusing genes together can be applied for combining the gene encoding the desired protein to the gene encoding the carrier protein. Furthermore the gene for the desired protein can be chemically synthesized and then fused to the carrier gene. This latter aspect is exemplified in Example 2 and 3 with insulin-like growth factor I (IGF-I) and part of IGF-I (IGF-57-70) which is a synthetically made gene coding for the 14 C-terminal amino acids of IGF-I. With the DNA synthesis technique genes for novel proteins (not found in nature) can be produced such as Z-protein.

As previously indicated the concept of this invention is based on the in vivo conjugation of a peptide antigen to an immunogenic carrier. The carrier is preferentially an IgG binding protein which may further enhance the immune response by its B-cell mitogenic activity (Sjödal et.al., Scand. J. Immunol. 10, 593, (1979)), its repetetive structure (Uhlén et. al., J. Biol. Chem. 259, 1695–1702 (1984)) and its ability to form complexes with immunoglobulins. In a preferred embodiment of the process of the invention the antigenic part contained within the hybrid protein is encoded by a cloned structural gene, parts thereof or synthetic oligonucleotides. The invention provides means by which antibodies (polyclonal, monoclonal) can be generated against any defined aminoacid sequence.

Another aspect of this invention concerns the use of the hybrid polypeptide as a vaccine, by designing a synthetic DNA segment encoding an antigenic region of natural protein from an infectious agent.

Generation of Polyclonal Antibody Against the Desired Amino Acid Sequence

The fusion protein containing the carrier protein fused to the desired amino acid sequence defined by a cloned or synthetic DNA segment is used to generate polyclonal antibodies in animals for instance rabbits, by standard well known techniques.

In summary, young rabbits are immunized subcutaneously and intramuscularly in the back with the fusion protein. The immunization is conducted periodically, and in various amounts to induce in vivo generation of an antibody directed against the desired peptide. Ideally the immunizations are conducted weekly with the initial immunization in 100–500 microgram doses and the remaining immunizations in 100 microgram doses. Rather than utilizing the fusion protein singularly, it may be mixed with complete or incomplete Freund's adjuvant. Ideally complete Freund's adjuvant is used in the initial immunization while the fusion peptide is emulsified in incomplete Freund's adjuvant for the remaining immunizations. Also, rather than injecting the entire volume of fusion protein in one body location, preferably on each occasion multiple injections are placed subcutaneously and intramuscularly in the back of the rabbits. At different time intervals, the rabbits are bled and serum samples tested for anti-peptide responses in an Electroblot assay. When the rabbit serum titer is high, the rabbits are bled and then the serum prepared, after allowing the blood to clot by high speed centrifugation. The immunoglobin G (IgG) fraction from the serum is then purified by standard techniques, such as by Protein A affinity chromatography or by use of ammoniumsulphate precipitation followed by DEAE-chromatograph. The purified IgG fraction can be used as one source of antibody for affinity purification of the hybrid protein molecules.

Preparation of Monoclonal Antibodies Against the Desired Peptide

The fusion protein, defined by the cloned DNA, may also be employed to generate monoclonal anti-peptide antibodies. The preferred procedure for generating the monoclonal anti-peptide antibodies is essentially as disclosed in U.S. Pat. No. 4,411,993, incorporated herein by reference. In the procedure, BALB/c mice are immunized with the purified fusion protein on several occasions at intervals of from 7 to 14 days. Various amounts of identification peptide are employed in each injection, ideally from 10 to 100 micrograms. In the initial injection, the peptide ideally is emulsified with complete Freund's adjuvant and in the subsequent inoculations, the peptide is emulsified in incomplete Freund's adjuvant. Rather than injecting the entire volume of fusion protein in one body location, on each occasion multiple injections are placed about the body of the mice, for instance, in the hind legs.

During the course of immunization, serum samples from the mice are tested by a RIA assay for an anti-peptide response. Once an antibody titer is detected, the animals are given an intraveneous injection of the identification peptide mixed with saline. Several days later the animals are sacrificed and their spleens harvested. Single cell suspensions from the splenocytes are cultured in tissue culture medium supplemented with various additives to expand the number of antibody producing cells. The antibody producing cells are isolated from the culture and purified by standard techniques for subsequent fusion with myeloma cells.

In the fusion process, the purified antibody producing spleen cells are mixed with murine Muridas-myeloma cells and then the mixture pelleted. Thereafter, a fusing agent is added to the cell pellet to facilitate fusion of the two different types of cells by centrifugation. Fusing agents may include various types of condensation polymers of ethylene oxide and water, such as polyethylene glycol (hereinafter "PEG") 1500. Other possible fusing agents include DNA transforming viruses, such as Sendai virus or the fusion protein obtained therefrom. For optimum fusion, the quantity and concentration of the fusing agent must be controlled. For instance, if PEG 1500 is used, this fusing agent should comprise about 40% (weight/volume). However, the volume PEG 1500 may range from 0.5 to 3 milliliters (ml) and the concentration of PEG 1500 may vary from 35% to 60% weight/volume of culture medium.

The cells are then resuspended in a tissue culture medium supplemented with various additives, and selected suppressing agents to preclude the growth of unfused myeloma cells, double myeloma hybrids, unfused spleen cells and double spleen cell hybrids thereby liberating the anti-peptide antibody producing monoclonal cells. Such growth inhibitors or suppressants may include hypoxanthine, aminopterin and thymidine (hereinafter collectively referred to as "HAT").

Filler cells are also added to the tissue culture medium to induce proliferation of the hybrid antibody producing cells. Although not yet definitely confirmed, it is considered that the filler cells function to provide optimum cell density to allow small numbers of hybrid cells to multiply more readily. Also, it is thought that the filler cells may provide the hybrid cells with nutrients required for their proliferation. Various types of filler cells may be employed, including thymocytes from the BALC/c mouse. Other types of filler cells include murine spleen cells, irradiated murine peritoneal exudate cells and murine macrophages. Although various concentrations of filler cells may be added to the culture medium, preferably the filler cells should be added to the HAT containing cultures in concentrations ranging from 0.5 to $5 \times 10^6$ cells per ml with an optimum density of about $3 \times 10^6$ cells per ml.

Rather than being grown as a single culture, the resuspended cells together with the growth medium, filler cells and selected suppressing agents are plated in multipe microtiter plates. After several days of culture, the hybridoma cells which are generated by this procedure are screened by RIA assay for anti-peptide antibody responses.

The hybrid cells which give positive results are harvested and cloned by a limiting dilution technique, as detailed in U.S. Pat. No. 4,411,993. In the limiting dilution procedure, anti-peptide antibody producing hybrid cells are individually cultured in vitro in medium containing filler cells and selected suppressing agents which prevent the growth of unfused spleen and myeloma cells. The cloning cultures which give rise to hybrid cell growth are screened by RIA assay for reactivity against the desired peptide.

The cloned hybridomas which produce antibody containing supernates reactive with the fusion peptide are harvested and the cultured in vitro larger volumes for bulk production. Alternatively, the anti-peptide antibody may be expanded in vivo by injecting the cloned hybridoma cells into the peritoneal cavity of mice and thereafter collecting the interperitoneal ascites which contain high concentrations of anti-peptide antibody. Applicants have found that the ascites fluid collected contains monoclonal anti-antibody at concentrations in excess of 3 mg per ml. The antibodies contained in the ascites fluid can be isolated and concentrated by established techniques, such as by differentiation ammonium sulfateprecipitation followed by gel column chromatography. If required, the antibody can be further purified by ion exchange chromatography and/or affinity chromatography based on the ability of the antibody to bind to protein A from *Staphylococcus aureus*. The polyclonal antibody, hybridoma supernates and monoclonal antibodies were tested for anti-peptide response in a Electroblot assay or in an immune radiometric assay (IRMA).

The invention will in the following be further illustrated by non-limiting examples with reference to the appended drawings, wherein:

K18: Rabbit immunized with synthetic IGF 57–70 chemically coupled to BSA (positive control).

K37: Rabbit immunized with protein A IGF-I genefusion.

K52: Rabbit immunized with ZZ-IGF 57–70 nonimmune serum was included as a negative control.

FIG. 6 shows the nucleotide and amino acid sequence of the ZZ-IGF-I encoded by the pEZZ-IGF-I plasmid vector. The regions encoding the signal peptide, the cleavage region, the two Z-regions and IGF-I are shown as well as restriction sites relevant for the construction strategy.

FIG. 8 shows schematically how the ZZ-P polypeptide or a IGB-peptide is purified using affinity chromatography.

Specific embodiments of the invention will now be described in detail.

STARTING MATERIALS

Bacterial hosts

Two different strains of *E.coli* K12 were used in the Examples:

HB 101 (Boyer, H. W. et.al. J.Mol.Biol., 41, 459–472 (1969) and JM 83 (Viera, J., et.al. Gene 19 259–268 (1982), *Staphylococcus aureus* SA113 (Uhlén et.al. (1984) J. Bacteriol 159, 713–719), (the strains are available at the Department of Biochemistry and Biotechnology, Royal Institute of Technology, Stockholm, Sweden).

CLONING VEHICLES

The cloning vehicles used in the Examples were pBR322 (Bolival, F. et.al., Gene 2, 93–113 (1977), pEMBL8 (Dente et.al., Nucl.Acids Res. 11, 1645 (1983), pRIT5, pRIT6 and pCH40 (Nilsson, B., et.al., EMBO J. 4 1075 (1985), pHL33, pEX4-IGF-I, pUC8-ZZ and pZZ-IGF-I (KabiGen Patent appln. 8505922-8 priority date Dec. 17, 1985, pUC8 (Viera, J., et.al. Gene 19 259–268 (1982).

Buffers and Media

Coating buffer: 1.59 g $Na_2CO_3$, 2.93 g $NaHCO_3$ and 0.2 g $NaN_3$, made up to 1 liter with distilled $H_2O$.

PBS: 8.0 g NaCl, 0.2 g $KH_2PO_4$, 2.9 g $Na_2HPO_4 \times 12-H_2O$, 0.2 g KCl made up to 1 liter with distilled $H_2O$ (pH 7.4).

PBST: 8.0 g NaCl, 0.2 g $KH_2PO_4$, 2.9 g $Na_2HPO_4$, $\times 12H_2O$, 0.2 g KCl, 0.2 ml Tween 20 and 0.2 g $NaN_3$ made up to 1 liter with distilled $H_2O$ (pH 7.4).

TSB: 30 g Tryptic Soy Broth, made up to 1 liter and autoclaved.

TBAB: 30 g Tryptic Blood Agar Base, made up to 1 liter and autoclaved.

ROUTINE METHODS

Certain procedures were carried out repeatedly in the Examples. Unless otherwise specified, they were done exactly as follows each time they were carried out. Methods routinely in molecular biology are not described (like the use of Commercial restriction enzymes, DNA-ligations, Bal 31 exonuclease, S1 nuclease and Klenow polymerase, polynucleotide kinase).

Transformations: Transformation of *E.coli* K12 with plasmid DNA was performed exactly as described (Morrison, D. A., Methods in Enzymology, Academic Press 68, 326–331 (1979). The transformants were selected in a conventional manner on plates (TBAB) containing 70 ml/l ampicillin.

Isolation of plasmid DNA: Plasmid DNA was isolated as described by Birnboim, H. C. et.al. Nucl.Acids Res. 7, 1513 (1979). Small scale preparations to screen a large number of transformants were made exactly as described by Kieser, T. Plasmid 12, 19–36 (1984).

Elution of DNA fragments: Elution of DNA fragments from either agarose or polyacrylamide gel pieces were performed exactly as described by Maxam et.al., P.N.A.S. (USA), 74, 560–564 (1977).

Ligation of DNA in Low Gel Temperature Agarose gel: Ligation directly in agarose gel was performed by running the electrophoresis in a Low Gel Temperature Agarose gel and after cutting out the band the gel piece was melted by heating to 65° C. After a 10 times dilution using Tris buffer (10 mM pH 7.4) ligation could be performed.

Detection and quantification of protein A: An ELISA test (Enzyme linked immunosorbent assay) was used to quantify protein A. The test makes use of a special microtiter plate (Titertek, Amstelstad, Netherlands) having no net charge. The wells are coated with human IgG (Kabi AB, Sweden) in a coating buffer. Test samples are added and protein A is bound to the Fc portions of the IgG adsorbed in the well. Protein A is then assayed by an anti-protein A (from rabbit) conjugated to beta-galactosidase (from Pharmacia AB, Uppsala, Sweden).

Assay: The wells of a microtiterplate are filled with 75 μl of a solution of human IgG at 16 ng/ml in Coating Buffer and the plate is incubated at room temperature for at least 1 hour. The wells are washed three times with 100 μl PBST and 50 μl of sample is added to each well. For quantitative determination 2-fold dilutions are made. After incubation for 1 hour the wells are washed 3 times with 100 μl PBST followed by addition of 50 μl anti-protein A beta-galactosidase (the amount of protein A binding capacity added to each well corresponds to the molar amount of IgG added to each well as detected by titration with protein A in excess). After incubation for 45 minutes, the wells were washed 3 times with 100 μl PBST followed by addition of 125 μl ONPG buffer. After incubation for 20–30 minutes 150 μl 0.1M NaOH was added to stop the reaction. The quantification is made by running a 2-fold dilution of a protein A standard solution of known concentration in parallel with the 2-fold dilutions of the test samples. The absorbance at 405 nm is measured for each well by a photometer.

SDS-PAGE: SDS-polyacrylamide gel electrophoresis was performed exactly as described by Laemmli, O.K. Nature (London), 227, 680–685 (1970) using a 10–20% step gradient gel.

Electroblot Assay

A purified preparation of the desired peptide was electrophoresed in a 10–20% polyacrylamide slab gel under reducing conditions using the discontinuous SDS buffer system as described by Laemmli, U.K. in Nature (London) 227, 680–685 (1970). The electrophoresis was run for three hours at 20 mA. After completion of electrophoresis the desired peptide was transferred to nitrocellulose USA 76, 4350–4354 (1979). The electrophoretic blot was incubated with 3.5% human IgG in phosphate buffered saline (PBS) at +37° C. for 1 hour in order to block remaining free protein binding sites. This is required for the specific immundetection employed.

Next, samples to be tested (animal serum containing polyclonal antibodies, monoclonal antibodies or hybridoma supernates) are diluted (ideally 1/50–1/1000) in phosphate buffered saline 0.01% NP40, 3.5% human IgG and incubated overnight at +4° C. with the electrophoretic blot. After rinsing the nitrocellulose blot in 3 changes of PBS, the detection of bound antibody is performed using the peroxidase anti peroxidase (PAP) system.

Rabbit anti mouse IgG or porcine anti rabbit IgG diluted 1:400 in PBS 0.01% NP40, 3.5% juman IgG were incubated for 1 hour at 37° C. with the nitrocellulose blots. The papers were rinsed in PBS, followed by incubation for 1 hour at 37° C. with a soluble complex of mouse PAP or rabbit PAP at a dilution of 1:1600. The blots were finally rinsed in three changes of PBS and stained for peroxidase activity in 50 mM Tris-HCl pH 7.6 containing 0.1 mg/ml 3'3'-diaminobenzidine (Sigma) and 0.01% $H_2O_2$. Colour development was stopped by transferring the nitrocellulose blots to a bath with deionized water.

IRMA Assay

Purified desired peptide is diluted to a concentration of approximately 25–50 μg/ml in 0.1M carbonate buffer pH 9.4. Approximately 75 μl was used to coat flexible PVC microtiter plates (Cooke Engineering). If the assay is being employed to detect reactivity against IGF-I a dilution of 50 μg/ml is used. After overnight incubation at +4° C., the wells were washed with PBS containing 0.5% BSA and 0.1% NP40 or with PBS containing 0.25% gelatin and 0.1% NP40.

Additional PBS containing either 0.5% BSA or 0.25% Gelatin is added to each well and then the microtiter plate is incubated at 37° C. for an additional 2 hour period to block all of the remaining sites in the well that have not already bound the desired peptide. The PBS thereby prevents nonspecific adherence of the antibody of interest to the wells. After this additional incubation, the PBS solution is decanted.

Next, samples to be tessted (animal serum containing polyclonal antibodies, nomoclonal antibodies or hybridoma supernates) are added to the wells and incubated for approximately 120 minutes at +37° C. After incubation, the antibody solutions are removed and each well repeatedly washed with PBS. Thereafter, approximately 50 μl of an iodine $^{125}$-labeled anti-immunoglobulin antibody is added to each well. If the assay is being employed to detect hybridoma supernates with anti-peptide reactivity, the $^{125}$I-labeled reagent is a rabbit anti-mouse antibody (Dakopatts A/S) at a specific activity of between 1–5μCi/μg approximately $3 \times 10^5$ cpm added/well.

If the assay is being employed to detect rabbit polyclonal antibody with anti-peptide reactivity, the $^{125}$Ila-beled reagent is a swine anti-rabbit IgG antibody (Dakopatts A/S) labeled to the same specific activity as above. Approximately $3 \times 10^5$ cmp is added to each well. The incubation is generally done overnight at +4° C. After repetetive washing with PBS, the microtiter wells are measured for their content of bound radioactivity in a gamma counter. The amount of bound radioactivity in the well is directly proportional to the quantity of antipeptide antibody in the well sample.

EXAMPLE 1

Figure 2:
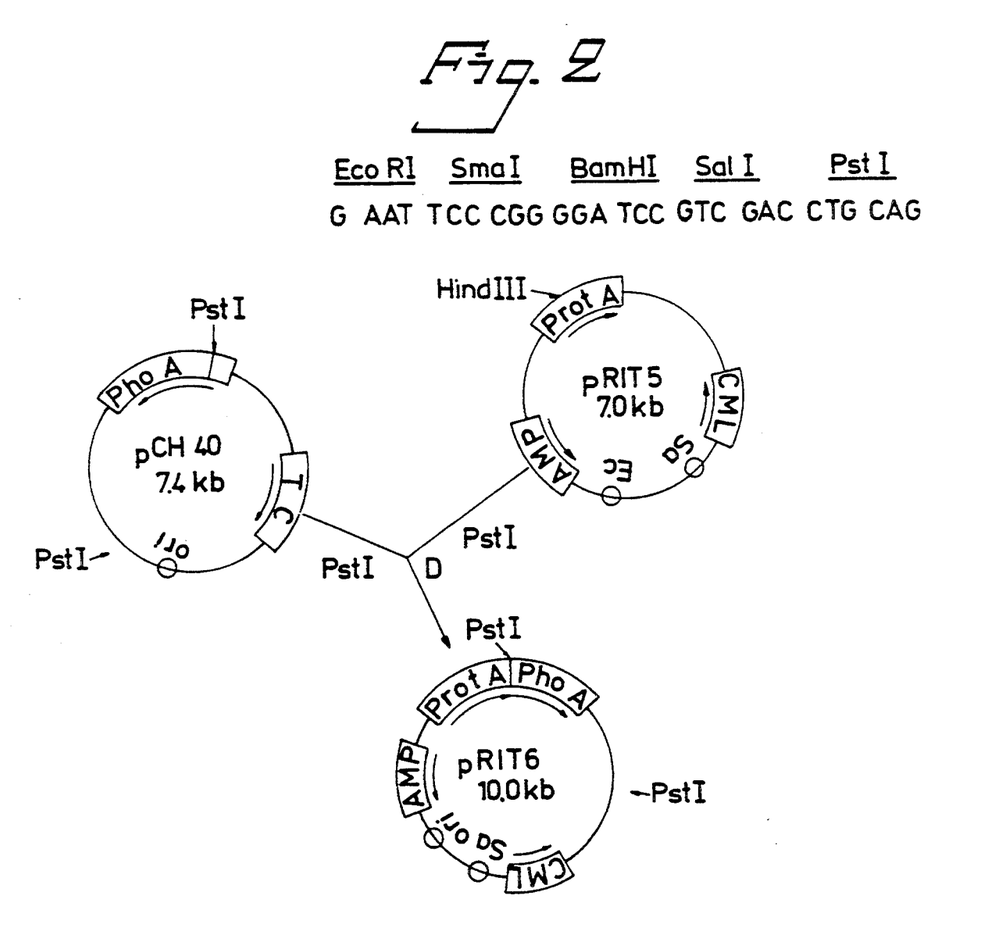
FIG. 2 shows the construction of pRIT6 by cloning the gene encoding alkaline phosphatase from pCH40, into pRIT5 as described by Nilsson, B., et. al. EMBO J. 4 1075–1080 (1985).

Preparation of Polyclonal Antibodies Against an Alkaline Phosphatase Protein A Gene Fusion The alkaline phosphatase gene from E.coli without its signal sequence was inserted into pRIT5 (FIG. 2) as described by Nilsson, B. et.al. in Embo, J. 4, 1075-1080 (1985) incorporated herein by reference. This resulting plasmid pRIT6 (FIG. 2) encodes a fusion protein consisting of the Nterminal 271 amino acid residues of the nature protein A, a linker region of 11 residues and the C-terminal portion of the alkaline phosphates, starting at residue 13. Plasmid pRIT6 was used to transform E.coli. For production of protein A-alkaline phosphatase the cells were grown in liquid medium containing 0.9% phosphate in order to repress endogenous alkaline phosphatase production. The protein A alkaline phosphatase fusion protein encoded by pRIT6 contains the protein A signal sequence and the hybrid should therefore be translocated through the cytoplasmic membrane of the transformed host cell. Measurements both on the protein A content (as described under routine method) and the alkaline phosphatase activity confirm that the fusion protein is found in the periplasm, establishing that a staphylococcal signal sequence can direct export of an enzyme in E. coli. Alkaline phosphatase activity was assayed by a colorimetric procedure using p-nitrophenyl phosphate (Sigma product No 104-0) in accordance with the supplier's recommendations).

For production of protein A alkaline gene fusion, the pRIT6 transformed E. coli cells were grown to a density of $A_{550}=1$. Thereafter the cells were lysed by sonication as described by Uhlén et.al. in Gene 23, 369-378 (1983). Alkaline phosphatase was subsequently purified from the cell lysate was passed through on IgG-Sepharose 4B column (Pharmacia, Sweden). The bound material was eluted with glycine buffer (0.1M pH 3.0), dialyzed against water and lyophilized.

For preparation of polyclonal antibodies against the fusion protein, two New Zealand rabbits were immunized by multiple site injections of 80 μg protein A-alkaline phosphatase emulsified in complete Freund's adjuvant. Two booster injections with the same amounts of protein were given 3 and 6 weeks after the initial immunization. The animals were bled after the last booster injection and after allowing the blood to clot overnight at +4° C., the serum was prepared by centrifugation 10 minutes at 3000 rpm. This serum was tested for reactivity against purified E. coli alkaline phosphatase (Sigma) as described under Electroblot assay. Both inoculated rabbits were found to produce antibodies with specific reactivity against alkaline phosphatase.

EXAMPLE 2

Preparation of Polyclonal Antibodies Against IGF-I Using a Protein A Genefusion

Construction of the fusion vector pUN201

The Synthesis and cloning of the gene encoding human IGF-I has been described elsewhere (Elmblad, A. et.al., in Third European Congress on Biotechnology III, 287-296, Verlag Chemie, Weinheim (1984).

The gene is contained on a 240 base pair EcoRI/Hind III fragment with the start codon (ATG) a few base pairs downstream from the EcoRI site and a (TAG) stop codon a few base pairs up stream of the Hind III site. The plasmid pUC8 with the IGF-I gene inserted in the EcoRI/Hind III sites was used to construct a shuttle vector (Nilsson, B., et.al., Nucl., Acids Res. 13 1151-1162 (1985)) allowing transfer between E. coli, B.subtilis and several staphylococcal species. The plasmid pC194 (Horinouchi, S., and Weisblum, B., J. Bacteriol 150 815-825 (1982)) containing a functional chloramphenicol resistance gene was cleaved with Hind III and inserted into the unique Hind III site of the pUC8-/IGF-I plasmid. The 1.1 kb EcoRI fragment from pSPA16 (Uhlén, M., Guss, B., Nilsson, B., Götz, F., and Lindberg, M., J. Bacteriol 159, 713-719 (1984)) containing the promoter, the signal sequence and the IgG binding regions of Staphylococcal protein A, was inserted in the unique EcoRI site of pUC8/IGF-I giving the plasmid pUN201.

The plasmid pUN201 has a truncated Staphylococcal protein A gene fused to the IGF-I gene. The fusion protein has a predicted molecular weight of 38.73.

The plasmid was introduced into S. aureus SA113 by standard protoplast transformation.

Expression, secretion and purification of the hybrid protein (prot A' IGF-I):

The hybird protein was efficiently expressed and secreted out into the medium of S. aureus. The extra cellular hybrid protein was chilled on ice and passed through an IgG-Sepharose-column. The bound material was eluted with 0.1M glycine buffer pH 3.0 dialayzed against water and lyophilized.

Polyclonal antibodies against IGF-I were prepared by immunization of New Zealand white rabbits with 200 μg of hybrid protein emulsified in Freund's complete adjuvant. The injections were given at multiple sites preferably intra-muscularly in the hind legs and subcutaneously between the shoulder blades. Two booster injections with 100-200 μg hybrid protein were emulsified in Freund's incomplete adjuvant and injected three and six weeks after the initial immunization. Blood was collected after the last booster injection by heart puncture serum was prepared by allowing the blood to clot overnight and then centrifuged 10 minutes at 3000 rmp, subsequently the serum was tested for reactivity against IGF-I by use of an IRMA assay as detailed earlier.

Figure 3:
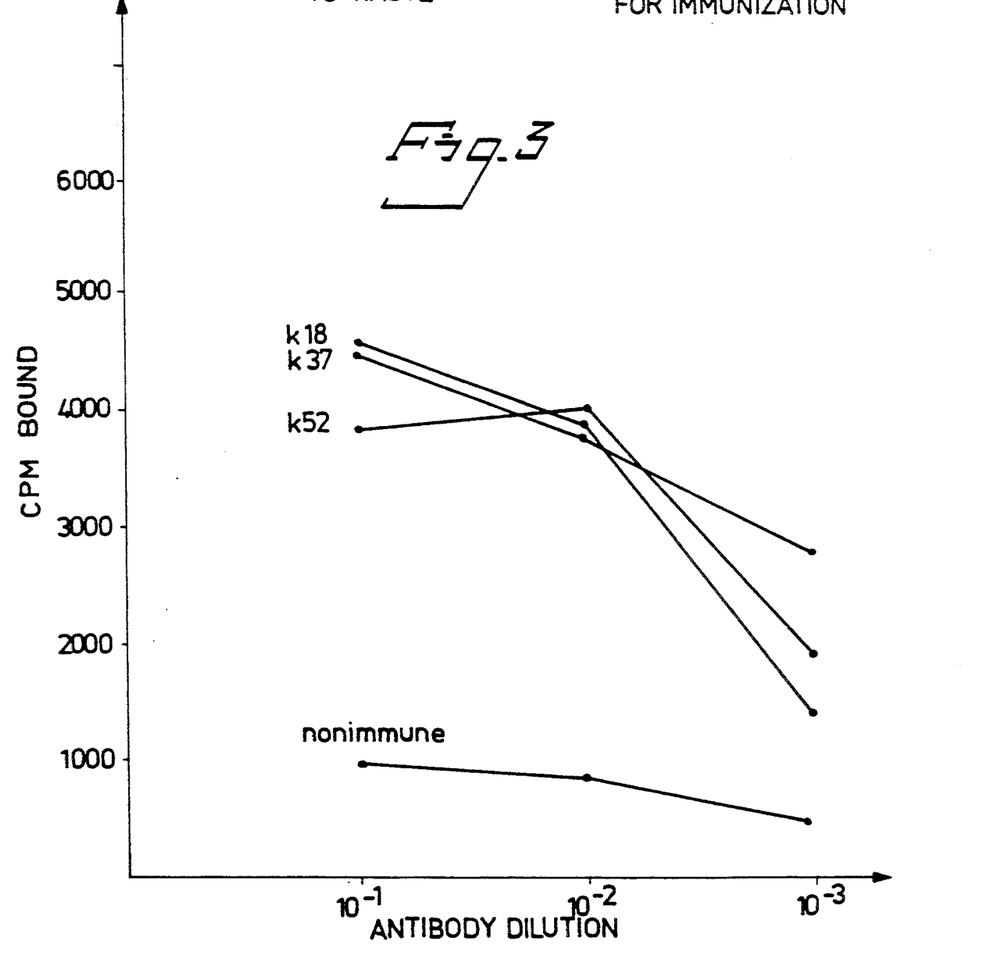
FIG. 3 shows a IRMA assay of different polyclonal rabbit antisera for reactivity against IGF-I. The assay was performed as described previously. Antibody dilutions were made in PBS containing 0.5% BSA (Sigma), 0.1% NP40 (K37, K52, nonimmune) or PBS, 0.25% Gelatin, 0.1% N40 (K18).

Rabbit K37 in FIG. 3 represents on rabbit immunized with the hybrid protein protein A-IGF-I assayed for antibody against native IGF-I protein in a comparison with two other polyclonal antibodies reactive with native IGF-I.

EXAMPLE 3

Preparation of Polyclonal Antibodies Against Peptide IGF 57-70 ZZ Genefusion

Synthesis and subcloning of the oligomers coding for amino acids 57 to 70 of IGF-I Two separate DNA oligomers, as shown in Table 1 were chemically synthesized as described by, for instance. (1) Letsinger et.al., 97 *Journal of American Chemical Society*, 3278 (1975); (2) Matteucci et.al. 21 *Tetrahedron Lett.*, and (3) Matteucci et. al. 103 *Journal of American Chemical Society*, 3185 (1981).

TABLE 1

| Oligomer 1 | 5'-AAT | TCT | CTG | GAA | ATG | TAC | TGC | GCT | CCG | CTG | AAA |
|---|---|---|---|---|---|---|---|---|---|---|---|
| Oligomer 2 | 3' | -GA | GAC | CTT | TAC | ATG | ACG | CGA | GGC | GAC | TTT |
| Amino Acide 57-70 of IGF-I | | | Leu | Glu | Met | Tyr | Cys | Ala | Pro | Leu | Lys |
| CCG | GCT | AAA | TCT | GCT | TAA G-3' | | | | | | |
| GGC | CGA | TTT | AGA | CGA | ATT GGT | AG-5' | | | | | |

TABLE 1-continued

| Pro | Ala | Lys | Ser | Ala | End. |
|-----|-----|-----|-----|-----|------|

The two oligomers in combination compose a termination codon (TAA) and compose a stretch of codons for the aminoacid sequence as indicated below the DNA sequence in Table 1.

This amino acid sequence constitutes the antigenic portion of the desired peptide (IGF 57–70). As shown in Table 1 where the two oligimers are combined, they define a terminus compatible with a EcoRI restriction endonuclease cleavage site and on the other end a terminus compatible with the restriction endonuclease cleavage site Bam HI.

Figure 4:
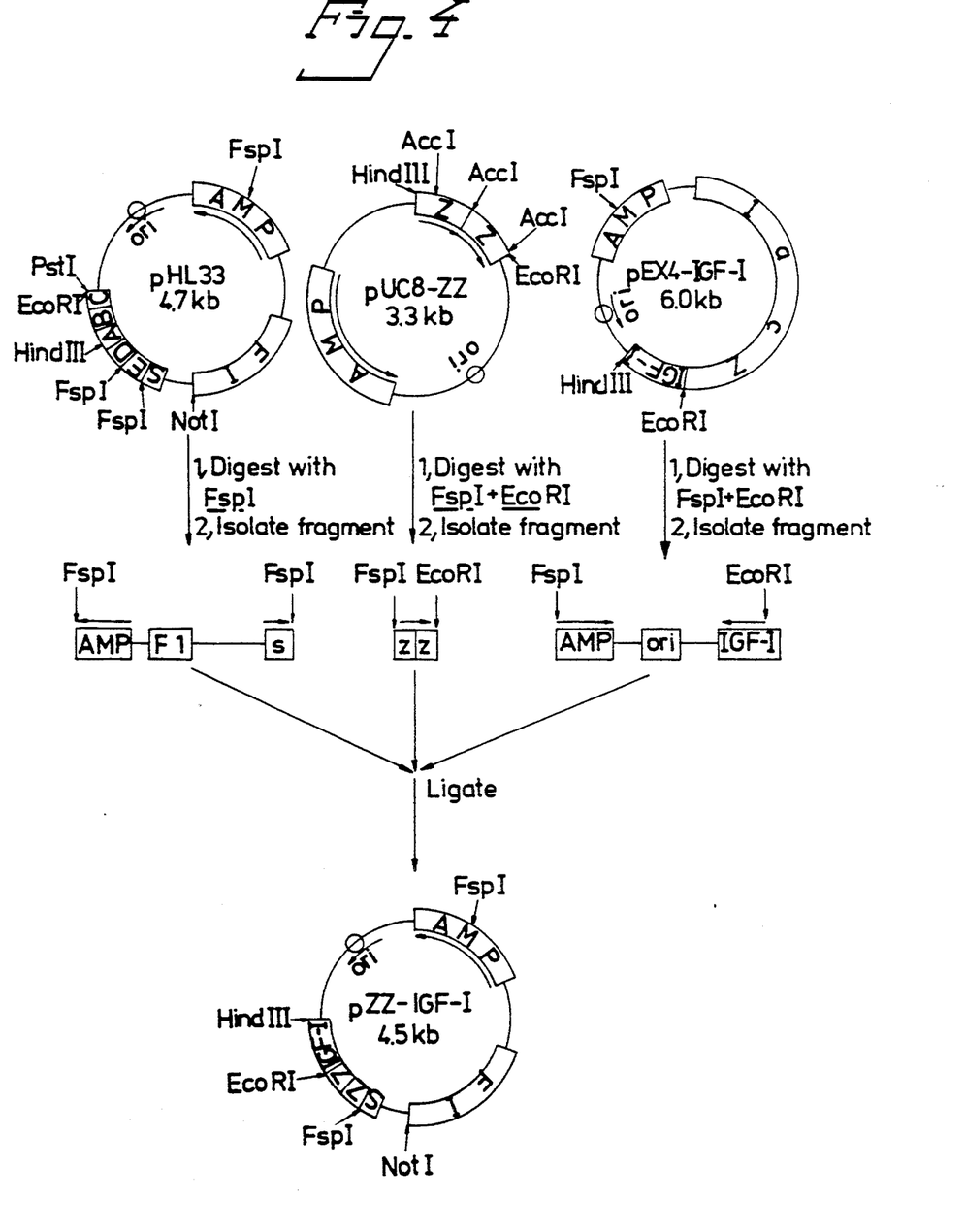
FIG. 4 shows the cloning strategy for the construction of pZZ-IGF-I as described in the Examples. AMP is the gene coding for beta-lactamase, S is the signal sequence, A-E are the IgG binding domains of protein A, ori is the origin of replication, Z is the synthetic fragment, IGF-I is the gene for IGF-I, F1 is the origin of replication from phage f1 and lacZ is the gene for beta-galactosidase.

The two oligomers were phosphorylated using the enzyme T4 DNA polynucleotide kinase and ATP as indicated in routine methods. 25 pmol of each of the oligomers were combined and hybridized in the kinase buffer by incubating the mixture at 75° C. and slowly during a period of approximately 1 hour lowering the temperature to ambient temperature. The cloning vector for the combined oligomers was pZZ-IGF-I described in FIG. 4. The construction of pZZ-IGF-I was made in the following way (FIG. 4). pUC8-ZZ (Kabi-Gen Patent Appln. 8505922-8 Priority date Dec. 17, 1985) was digested with Fsp I and Eco RI and the smallest fragment was isolated on LGT agarose. The plasmid vector pHL33 was digested with FspI. The largest fragment (2273 bp) was isolated on LGT agarose. The plasmid pEX4-IGF-I was digested with Fsp I and Eco RI. The small fragment spanning over the IGF-I gene into the AMP gene was isolated. The three fragments from A, B and C were ligated together as described in Routine Methods and the ligation mixture was transformed into E. coli JM83. Transformant selection was conducted using a LB agar medium containing 70 µl/ml of ampicillin. Isolation of the plasmid DNA and analysis with restriction enzyjmes confirmed that the transformants carried the plasmid pZZ-IGF-I.

The plasmid pZZ-IGF-I was digested with Eco RI and Bam HI and purified on low gel temperature (LGT) agarose. A portion of the purified plasmid fragment from pZZ-IGF-I and (0.0 pmol) and 6 pmol of the hybridized oligomers were mixed and ligated in 50 µl. The mixture was used for transforming competent cells of E. coli. Transformant selection was conducted on TBAB plates containing 50 µg/ml of ampicillin.

The colonies obtained were further analyzed by immunoblot analaysis using K18 rabbit serum (for reference on K18 see FIG. 3) for the detection of IGF-I antigen and nonimmune serum for detection of the ZZ protein. Two of the positive colonies identified by the immunoblot technique were further analaysed by restriction mapping. The cells containing the plasmid were grown in 500 ml scale and the ZZ57–70 hybrid protein was purified using affinity gel chromatography (IgG-Sepharose).

The protein was analysed using SDS-gelelectrophoresis and western blot analysis. Plasmid DNA from these two positive strains were purified using standard procedures.

Figure 5:
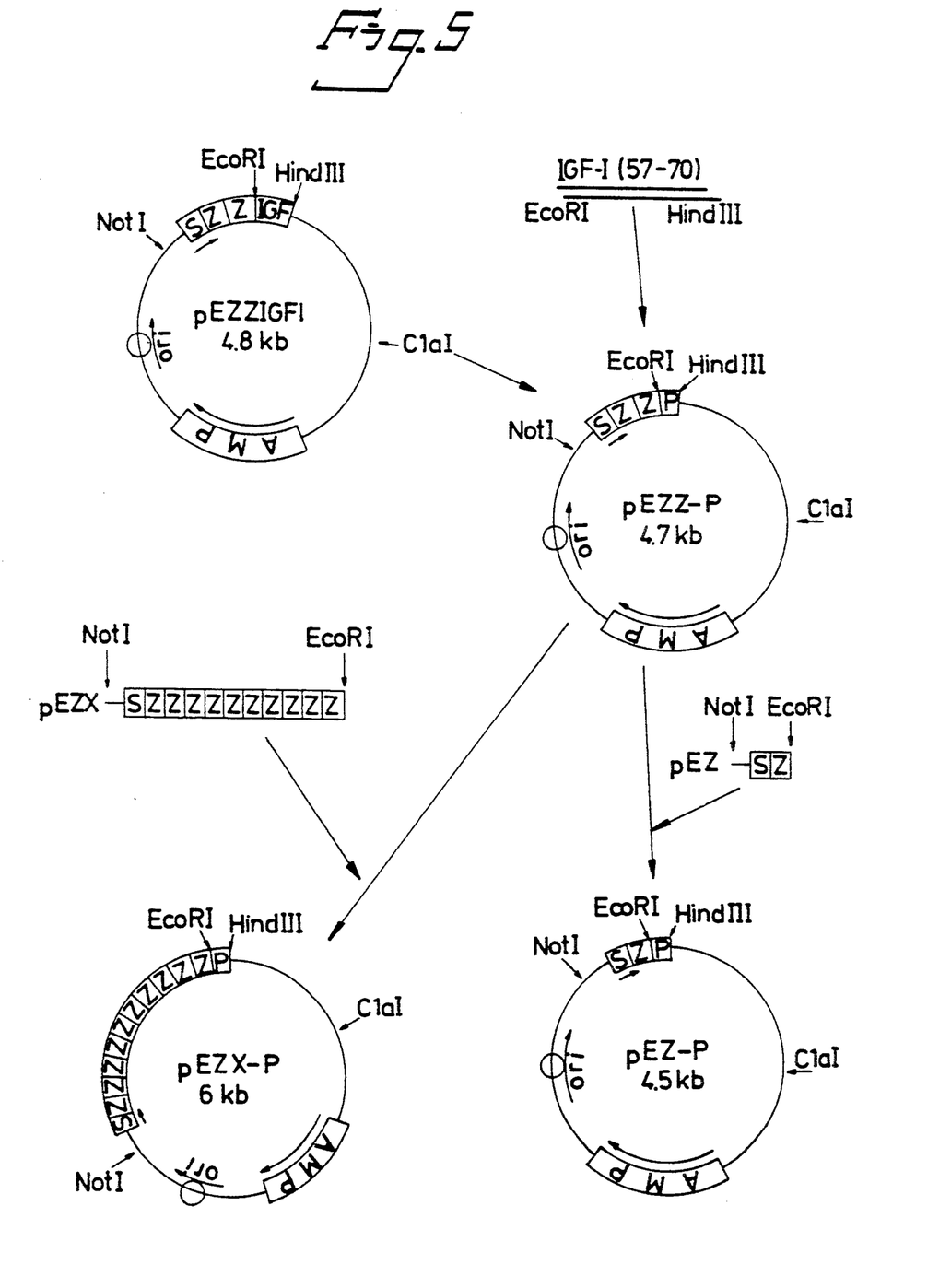
FIG. 5 shows the cloning strategy described in Examples 2 and 3. Amp is the gene coding for beta-lactamase, S is the signal sequence, Z is the synthetic fragment, IGF-I is the gene for IGF-I.
Figure 7:
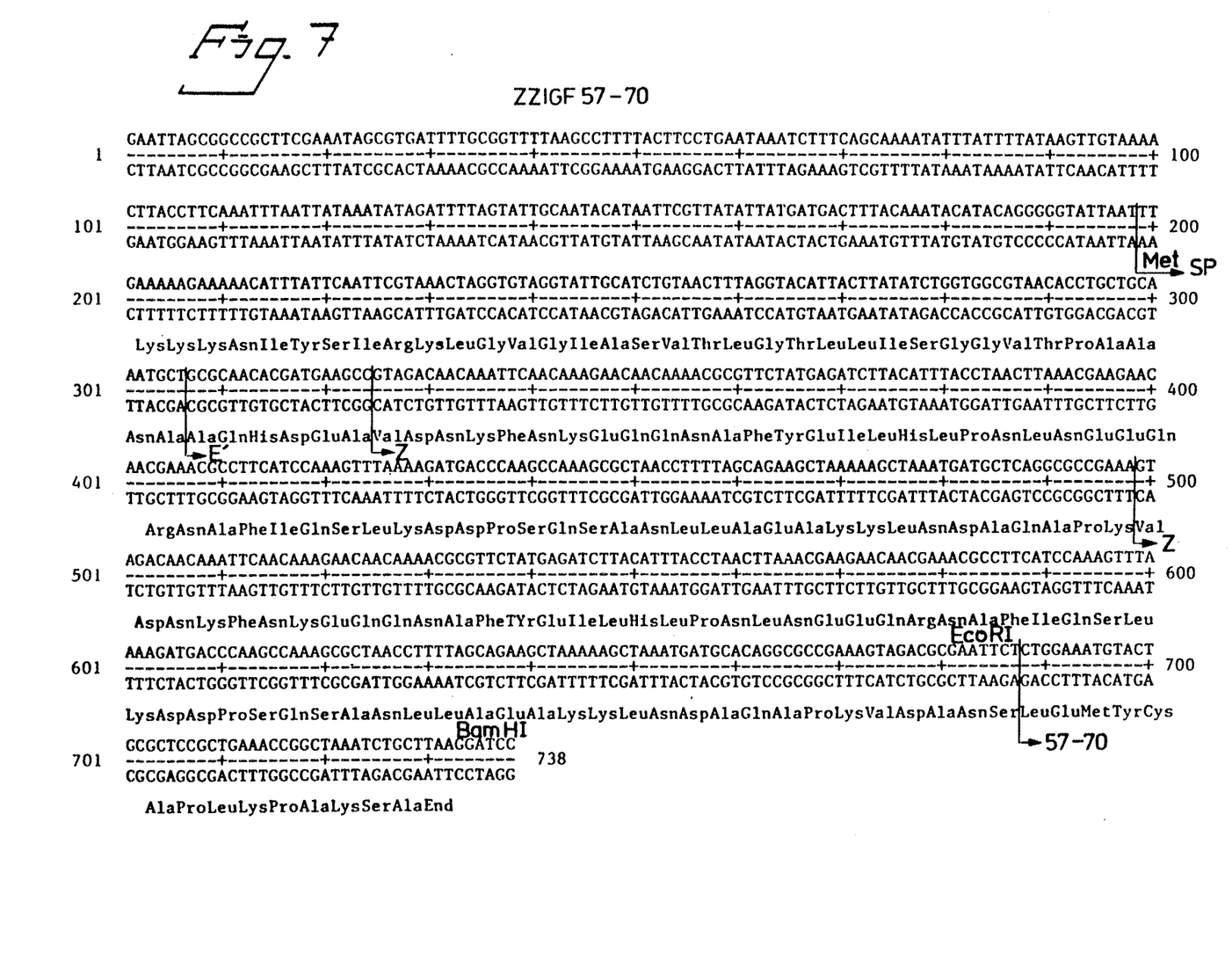
FIG. 7 shows the nucleotide and amino acid sequence of the ZZ-IGF 57–70 encoded by the pEZZ-IGF-P plasmid vector. The regions encoding the signal peptide, the two Z-regions and 57–70 amino acid sequence are shown as well as restriction sites relevant for the construction strategy.

The plasmid DNA was digested with Eco RI and Hind III, cleaving out the whole of the IGF-57–70 insert together with part of the pUC8 cassette Bam HI to Hind III. This Eco RI, Hind III fragment was transferred to the vector pEZZ-IGF-I as described below (FIG. 5).

Construction of the plasmid vector pEZZ-IGF-I

The plasmid vector pZZ-IGF-I was the starting material for the construction. The gene fragment spanning the promoter, signal sequence, the two Z regions and the IGF-I gene was cleaved out using the restriction endonucleases Not I and Hind III. The fragment was cloned in pEMBL8 (Dente et.al., Nucl. Acids. Res., II, 1645 (1983)), where the Eco RI restriction site previously has been linked to a Not I site, in Not I/Hind III.

The resulting plasmid, designated pEZZ-IGF-I, is directing high extracellular expression of the ZZ-IGF-I polypeptide when introduced in E. coli.

Cloning of the synthetic linker encoding the amino acid sequence 57–70 of IGF-I into the expression plasmid pEZZ The synthetic linker encoding the immunogenic peptide (P) was cloned into pEZZ-IGF-I by replacing the IGF-I gene with the synthetic linker fragment Eco RI to Hind III as described above. The resulting plasmid vector was designated pEZZ-P and encodes two Z regions fused to the peptide 57 to 70 of IGF-I (hereinafter called Peptide) (FIG. 5).

In the pEZZ-IGF-I construct the Z region was to be polymerized at gene level. This can be achieved by a cleavage with Acc I and a religation. In this way the Z fragment is cleaved out getting different sticky end sequences in the "head" and "tail" end of the Z gene respectively. This ensures a head-to-tail ligation of the Z fragments. The plasmid vector pEZZ-IGF-I was cleaved with Acc I and the Z fragment and the vector fragment were recovered from an agarose gel. The purified Z fragment was ligated for 20 minutes prior to the addition of the vector fragment allowing for polymerization. After transformation selection for halos on agar plates containing dog serum was made. To get precipitation halos around the colonies on dog serum plates two or more Z fragments are needed. By isolating plasmid DNA from clones giving halos followed by restriction analaysis, clones from two up to ten Z fragments could be isolated.

The Not I/EcoRi restriction fragment spanning the promoter and the ten Z fragments was cloned into the pEZZ-P (Not I/EcoRI) replacing the ZZ fragment. The resulting plasmid vector, designated pEZX-P, codes for ten Z regions fused to the peptide.

To get the gene fragment ZZ replaced by Z the plasmid vector pEZZ-P was cleaved with Not I/Eco Ri and a Z fragment from the plasmid vector pASZ2 (KabiGen Patent Appln. 8505922-8 Priority date Dec. 17, 1985 was ligated to this construction giving the vector pEZ-P.

Expression and purification of the antigen

The antigens Z-P, ZZ-P and ZX-P (where P stands for the Peptide) were all prepared in the same way. The E. coli HB 101 strains containing the plasmid vector pEZ-P, pEZZ-P and pEZX-P respectively were grown in a 2 liter lab bench fermentor.

After fermentation at 37° C. during exponential growth the temperature was switched to 42° C. in the beginning of the stationary growth phase, and after 2 hours at 42° C. the fermentor was cooled to 10° C. After centrifugation the growth media was run through an IgG-sepharose column (Pharmacia, Uppsala, Sweden). The column was wasted with 5 bed volumens of Tris buffer containing salt (50 mM Tris pH 7,4, 150 mM NaCl) and the product was eluted using 1M HAc titrated to pH 2.8 using NH4Ac. The eluted material was lyophilized, and was ready to be used for immunization see FIG. 8.

New Zealand white rabbit were initially immunized with 200 μg of the ZZ-IGF-57-70 fusion protein emulsified with Freund's complete adjuvant by intramuscular and subcutaneous injections at multiple sites preferably in the hind legs and between the shoulderblades.

Three additional booster injections with the same amount of protein emulsified in Freund's incomplete adjuvant, were given 3 weeks after the first injection with one week intervals. Blood samples from injected animals was drawn from an ear vein after the third booster and serum was prepared by allowing the blood to clot overnight at +4° C. followed by 10 minutes centrifugation in an Eppendorf centrifuge at 12,000 rpm.

Serum was tested for the presence of antibody reactive against IGF-I by use of an IRMA assay as detailed previously. Rabbit K52 in FIG. 3 represents one rabbit immunized with the hybrid protein ZZ-IGF-I-57-70 assayed for the presence of antibodies reactive with the native IGF-I protein in a comparison with two other polyclonal antibodies reactive with native IGF-I. The result demonstrate that the specific antibodies obtained against the hybrid protein recognize native IGF-I.

We claim:

1. A process for preparing polyclonal antibodies specific for an amino acid sequence comprising the steps of (i) immunizing a mammal with a fused protein comprising said amino acid sequence fused to an immunogenic IgG binding protein, said fused protein being prepared by a process comprising the steps of (A) introducing a cloned or synthetic DNA segment encoding said amino acid sequence into a procaryotic expression vector, wherein said DNA segment is fused to a gene encoding said immunogenic IgG binding protein, (B) transforming a procaryotic host cell using such expression vector, and (C) allowing said host cell to express the fused protein and (D) recovering same, said IgG binding protein providing recognition of said amino acid sequence by an immune system of an inoculated mammal; (ii) bleeding said immunized mammal to obtain serum; and (iii) recovering generated antibodies from said serum.

2. A process according to claim 1, wherein said expression vector is a plasmid.

3. A process according to claim 1 wherein said DNA segment encoding said amino acid sequence is introduced into said expression vector by digestion of the expression vector with an appropriate restriction enzyme and joining said DNA segment to said expression vector.

4. A process according to claim 1, wherein the IgG binding protein is S. aurens protein A.

5. A process according to claim 1, wherein both the amino terminal end and the carboxyl terminal end of said amino acid sequence are fused to the IgG binding protein.

6. A process according to claim 1, wherein the mammal is selected from rabbits and mice.

7. A process according to claim 2, wherein said DNA segment encoding said amino acid sequence is introduced into said plasmid by digestion of the plasmid with an appropriate restriction enzyme and joining said DNA fragment to said plasmid.

8. A process according to claim 2, wherein a synthetic DNA segment encoding an antigenic determinant of a natural protein is introduced into an said plasmid and is fused therein to a gene encoding said IgG binding protein.

9. A process according to claim 2, wherein both the amino terminal end and the carboxyl terminal end of said amino acid sequence are fused to the IgG binding protein.

10. A process for preparing monoclonal antibodies specific for an amino acid sequence comprising the steps of (i) immunizing a mouse with a fused protein comprising said amino acid sequence fused to an immunogenic IgG binding protein, said fused protein being prepared by a process comprising the steps of (A) introducing a cloned or synthetic DNA segment encoding said amino acid sequence into a procaryotic expression vector, wherein said DNA segment is fused to a gene encoding said immunogenic IgG binding protein, (B) transforming a procaryotic host cell using such expression vector, and (C) allowing said host cell to express the fused protein and (D) recovering same, said IgG binding protein providing recognition of said amino acid sequence by an immune system of an inoculated mouse; (ii) upon detection of an antibody titer in the serum of said immunized mouse, harvesting the spleen of said mouse; (iii) isolating antibody producing cells from said spleen: (iv) fusing said antibody producing spleen cells with mouse myeloma cells to generate hybridoma cells; (v) harvesting hybridoma cells which produce antibody reactive with said fusion protein and (vi) recovering said antibodies from said harvested hybridoma cells.

* * * * *